United States Patent [19]

Garito et al.

[11] Patent Number: 4,463,759

[45] Date of Patent: Aug. 7, 1984

[54] UNIVERSAL FINGER/FOOT SWITCH ADAPTOR FOR TUBE-TYPE ELECTROSURGICAL INSTRUMENT

[76] Inventors: Jon C. Garito, 22 Deering La., East Rockaway, N.Y. 11558; Alan Ellman, 1 Auerbach La., Lawrence, N.Y. 11516; Zvi Rozensher, 1135 Railroad Ave., Hewlett, N.Y. 11557

[21] Appl. No.: 339,171

[22] Filed: Jan. 13, 1982

[51] Int. Cl.³ ............................................. A61B 17/39
[52] U.S. Cl. ........................... 128/303.14; 128/303.17; 307/117
[58] Field of Search ..................... 128/303.13, 303.14, 128/303.17, 303.18; 307/117

[56] References Cited

U.S. PATENT DOCUMENTS

| | | | |
|---|---|---|---|
| 3,801,800 | 4/1974 | Newton | 128/303.14 X |
| 4,071,028 | 1/1978 | Perkins | 128/303.14 |
| 4,092,986 | 6/1978 | Schneiderman | 128/303.14 |
| 4,318,409 | 3/1982 | Oosten | 128/303.14 |
| 4,334,539 | 6/1982 | Childs et al. | 128/303.14 |

*Primary Examiner*—Lee S. Cohen

[57] ABSTRACT

A novel self-powered control unit for interfacing a tube-type electrosurgical mainframe to a finger-switch handpiece comprises completely-isolated electrical circuitry for preventing harmful feedback from mainframe to handpiece, a control function in parallel with the conventional mainframe footswitch, and novel battery-monitoring circuits for testing battery status.

13 Claims, 2 Drawing Figures

UNIVERSAL FINGER/FOOT SWITCH ADAPTOR FOR TUBE-TYPE ELECTROSURGICAL INSTRUMENT

This invention relates to a novel control unit for an electrosurgical instrument, and in particular to a plug-in adaptor that can be retrofitted to existing tube-type electrosurgical instruments for accommodating existing plug-in finger switch handpieces for finger and foot control of the instrument.

BACKGROUND OF THE INVENTION

There already exist on the marketplace and in use a number of electrosurgical instruments which employ electron tubes to generate the desired radio-frequency (RF) currents. Ellman U.S. Pat. No. 3,730,188, whose contents are herein incorporated by reference, discloses one form of instrument that has been in wide use for many years. In the circuitry described in this patent, when the power ON-OFF switch on the instrument front panel is thrown ON, power from the conventional alternating current (AC) source or line activates the direct current (DC) power supply for the RF generator and turns ON the filament circuit for the electron tube used in the RF oscillator section to generate the RF currents. The choice of currents available for cutting, coagulation or fulguration is determined by a rotary switch on the instrument front panel which selectively introduces rectifiers and capacitors into the DC power supply circuit to control the waveform of the DC voltage applied to the plate and screen grid of the tube. However, in this standby mode, no RF currents are actually generated because the tube's cathode circuit to ground remains open due to the series connection of a normally-open foot switch which is plugged into a jack on the instrument's front panel. To place the unit in its operating mode, the user (dentist or doctor) presses the foot switch. This closes the tube's cathode circuit and, since the cathode filament is hot, immediately causes conduction through the tube activating the RF oscillator. The RF currents thus generated are conducted via a cable plugged into a jack on the instrument front panel to the handpiece held by the user and to the probe tip, which now may be applied by the user to the patient to perform an electrosurgical procedure. Releasing the foot switch returns the unit to its standby mode.

Recently, there has come on the market modified handpieces with built-in or incorporated finger switches which function to switch power delivery to the handpiece tip thus eliminating the foot switch. One such unit is described in U.S. Pat. No. 4,034,761. A commercial version is fitted at the cable end with a 3-pin plug connector adapted to plug into three similarly configured jacks on the instrument front panel. One pin carries the RF current, and the remaining two pins perform the instrument ON-OFF switch function controlled by one or two finger switches on the handpiece.

U.S. Pat. No. 4,071,028 describes a typical solid-state instrument usable with this new finger-switch handpiece. It comprises three separable units: The mainframe containing a solid state RF generator and power supply therefor, a control unit that plugs into the mainframe, and the finger-switch handpiece with cable that plugs into the control unit. The foot switch is eliminated. The control unit contains a light-emitting diode (LED) and battery in series with the finger switch. When the user actuates the finger switch, the battery turns on the LED. The LED light, detected by a photoconductor to form a photon coupled isolator, in turn turns on a power TRIAC whose anode-cathode circuit is connected in series with the AC line leading to the mainframe. This, in turn, conducts AC power from the line into the mainframe, turning on the solid-state RF generator, whose current is conveyed via the control unit to the handpiece.

The above-described combination is not suitable for use with a tube-type RF generator, because if connected to a tube mainframe, a delay in the production of the RF currents would ensue as a result of the delay in heating of the tube filaments. It typically takes about 30 seconds warm-up time before the tube filaments reach operating temperature and sufficient tube conduction results to sustain the RF oscillations. A user cannot efficiently use such a combination if he must wait 30 seconds after operating the finger switch before the handpiece can be applied to the patient.

SUMMARY OF THE INVENTION

An object of the invention is a universal adaptor or control unit to interface between most finger-switch handpiece probes and a tube-type electrosurgical mainframe.

Another object of the invention is a control unit interface between a tube-type electrosurgical mainframe and a finger-switch handpiece probe that does not eliminate the foot switch and allows use of either the foot switch or the finger switch, at the user's option, to switch the mainframe from its standby to its operating mode.

Still another object of the invention is a self-powered control unit for interfacing a tube-type electrosurgical mainframe to a finger-switch handpiece probe and which provides complete electrical isolation between the AC line voltage and high DC voltages typically present in such a mainframe and the handpiece to prevent possible harm to the patient or user.

Still a further object of the invention is a battery-operated control unit interface between a tube-type electrosurgical mainframe and a finger-switch handpiece and which provides a reliable status indication of the battery condition to warn the user when battery replacement is necessary to ensure proper execution of the electrosurgical procedure.

These and other objects and advantages of the invention as will appear hereinafter are achieved with a novel self-powered control unit that is adapted to plug into the jacks of most tube-type mainframes and is in turn provided with suitable jacks for receiving the plug at the cable end of a conventional finger-switch handpiece probe. The novel control unit is provided with circuitry to perform the following functions:

1. The handpiece finger switch when actuated provides a connection in parallel with the existing ON-OFF foot switch connected to the mainframe. Thus, the mainframe standby mode, with heated tube filaments, is established when the mainframe ON-OFF switch is thrown into the ON position, and conversion to the operating mode and generation of RF currents occurs instantaneously when either the finger switch or foot switch is actuated.

2. Complete electrical isolation is afforded between the handpiece and the high voltages in the mainframe necessary to operate the tube RF oscillator to prevent harm to the patient.

3. A battery monitoring circuit is provided to warn the user when battery voltage falls below a desired level which may affect proper operation of the control unit to ensure replacement of the battery before interfering with the electrosurgical procedure.

The invention will now be described in detail with respect to a preferred embodiment thereof, which should be read in conjunction with the accompanying drawings.

DESCRIPTION OF A PREFERRED EMBODIMENT

Figure 1:
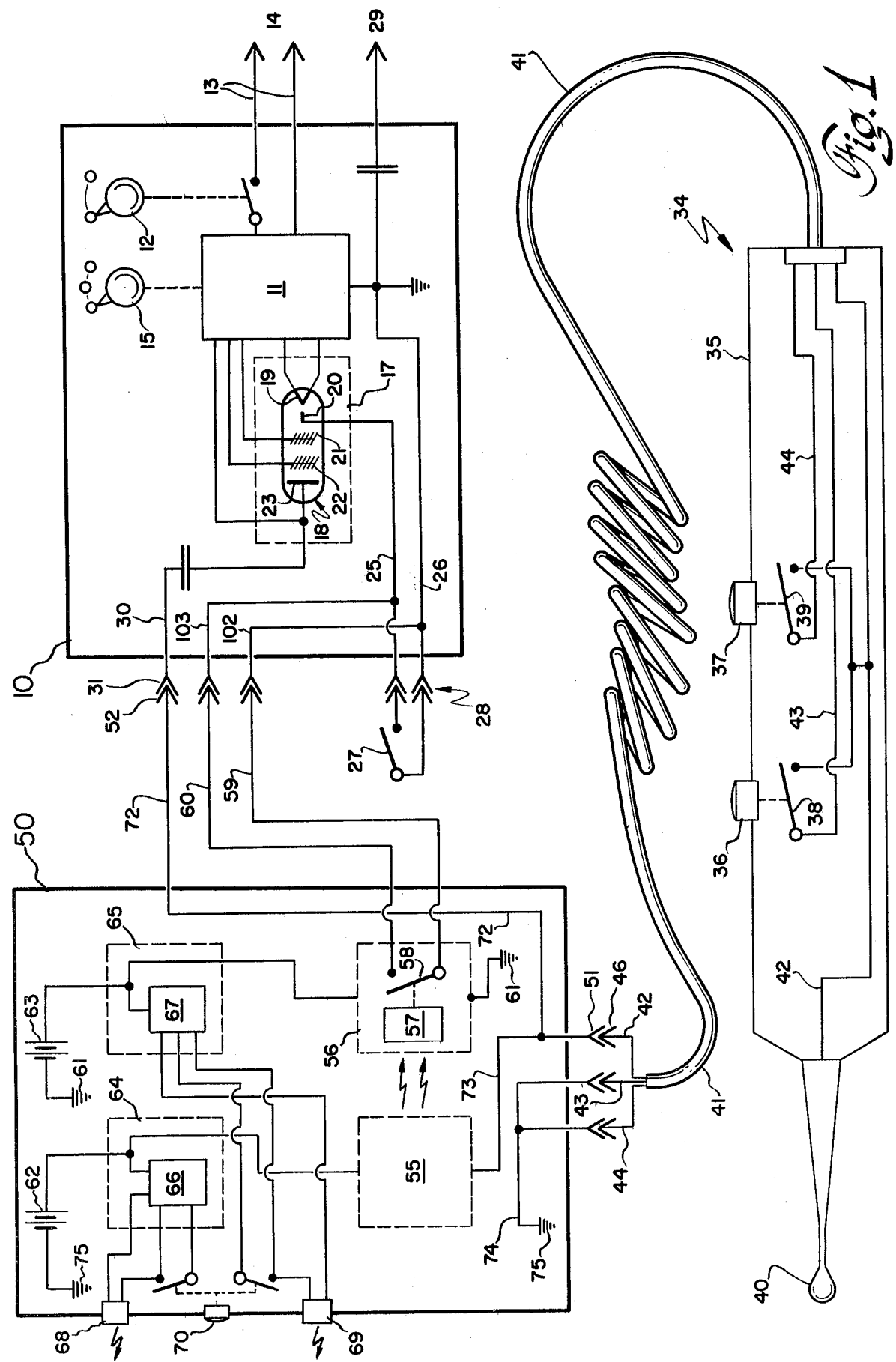
FIG. 1 is a schematic view illustrating a conventional mainframe electrosurgical instrument, a conventional finger-switch handpiece probe, and one form of control unit in accordance with the invention for interfacing the mainframe to the handpiece.

Referring now to the drawings, FIG. 1 illustrates a mainframe electrosurgical instrument 10 of the type described in FIG. 1 of U.S. Pat. No. 3,730,188, which is capable of generating a fully-rectified current for cutting, a partially rectified current for combined cutting and coagulation, and a half-wave rectified current for coagulation. These various currents are obtained by operating a 3-position control knob on the front panel which selectively switches in ground, a resistor and an open circuit in the DC power supply which converts the AC line voltage to suitable DC voltages for activating the electron tube which forms the active part of the RF oscillator circuit of the RF generator. The tube would have the usual filament supply (not shown in the patent) for heating the tube cathode to operating temperature. In FIG. 1 of the present drawing, the power supply is indicated by block 11, connected by way of an ON-OFF switch 12 on the front panel through the line cord 13 to the usual outlet supplying AC line voltage 14. The three-position RF current control switch described above is shown at 15. The RF generator, depicted by block 17, contains the electron tube 18 with heating filament 19, cathode 20, control grid 21, screen grid 22 and anode 23. The remaining oscillator circuit components have been omitted for clarity. The tube cathode 20 is grounded via conductors 25 and 26 through an external foot switch 27 which plugs in via 2-pin connector 28 into the mainframe 10. The indifferent electrode for providing RF patient ground is indicated by numeral 29. When the ON-OFF switch 12 is placed in the ON position, the power supply 11 is activated and the tube filament 19 heated, placing the mainframe 10 in its standby mode, but no RF currents are generated because the tube's cathode circuit is open. When the foot switch 27 is closed by the user, the cathode circuit is completed and the RF oscillator circuit breaks immediately into oscillation and RF currents are generated, as controlled by front panel switch 15, and conducted via conductor 30 to one jack of a 3-jack mainframe connector 31 on the front panel. This represents the operating mode of the mainframe.

A conventional two finger-switch handpiece probe is illustrated at 34. It comprises an elongated hollow body 35 containing on top first 36 and second 37 finger buttons for actuation by the user. The buttons 36 and 37 when pressed actuate, respectively, switches 38 and 39 inside the body 35. The left end of the body is fitted with an electrode 40, and a 3-wire cable 41 is connected at the right end. One cable wire 42 is connected to the electrode 40 and one side of each of the switches 38, 39. The remaining two wires 43, 44 are connected to the other side of each of the switches. The cable 41 terminates in a 3-pin handpiece connector 46.

One form of control unit 50 in accordance with the invention interfaces the handpiece 34 to the main frame 10. The control unit comprises a first 3-jack connector 51 for receiving the handpiece connector 46, and a second 3-pin connector 52 for plugging into the mainframe connector 31. The control unit further comprises a first circuit 55 containing a light-emitting device, such as an LED (the jagged arrows indicate emitted light), and a second independent circuit 56 containing a light-responsive device 57 which when receiving light from the LED operates a switch 58 connected via conductors 59, 60 across two of the plugs of second connector 52. The first and second circuits are powered by separate respective batteries 62, 63 through separate third 64 and fourth 65 battery-monitoring circuits. Each of the battery-monitoring circuits has an active device 66, 67, respectively, connected to a light-emitting device, respectively 68, 69, through a common push-button 2-pole switch 70. The third plug of second connector 52 is connected via conductor 72 to one jack of the first connector 51, which is also connected via conductor 73 to the first circuit 55. The remaining two jacks of first connector 51 are grounded at a first ground 75 via conductor 74. The second circuit 56 has a second ground connection 61, shared with the fourth circuit 65. Similarly, the first 55 and third 64 circuits share a common ground 75. The first and second DC grounds 75 and 61 are not connected together but are isolated from each other as well as from the main frame ground represented by indifferent electrode 29.

Figure 2:
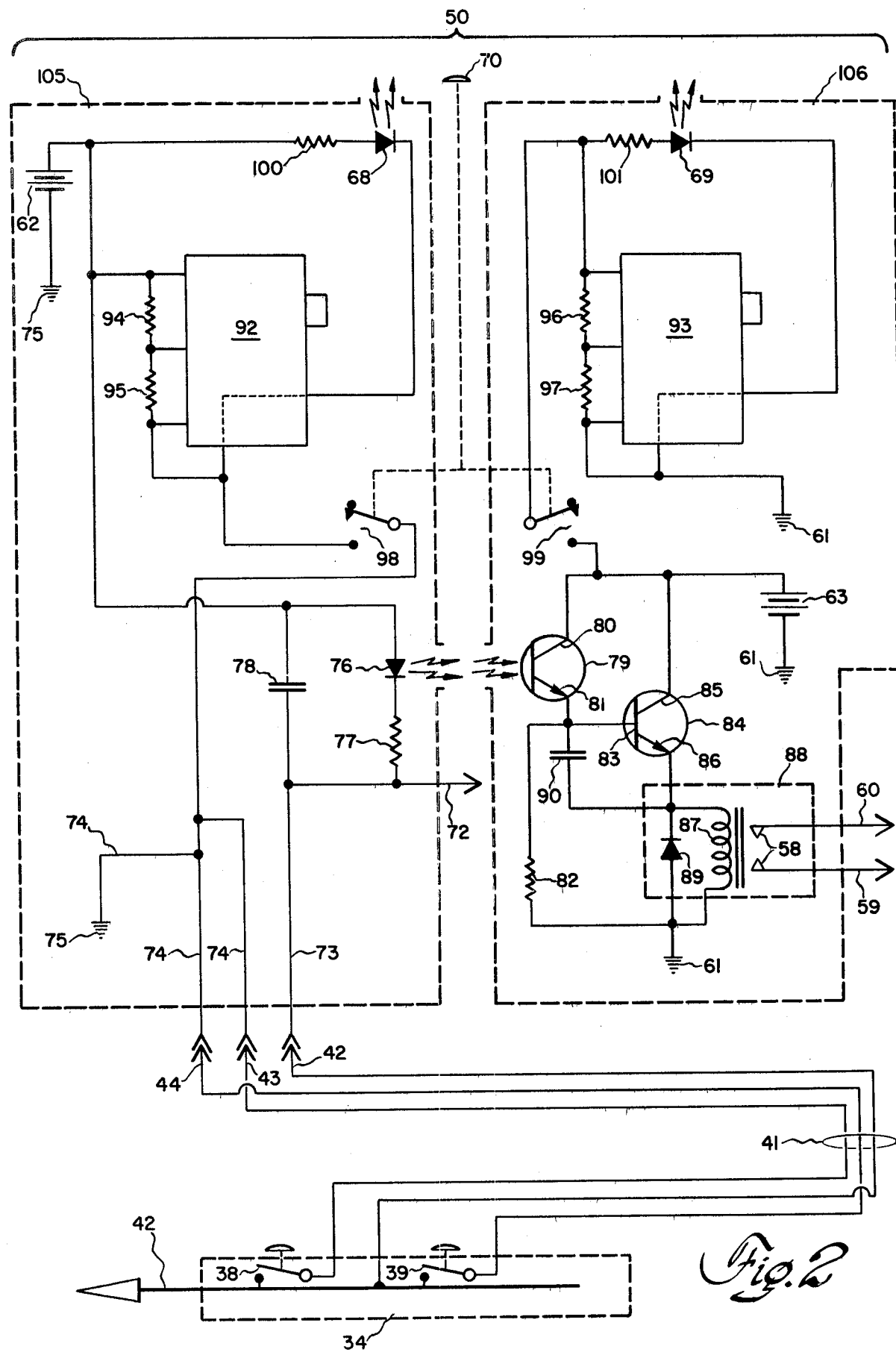
FIG. 2 is a circuit schematic of the control unit and handpiece of FIG. 1.

A detailed circuit schematic for control unit 50, including the handpiece, is illustrated in FIG. 2, with the same reference numerals designating the same elements. The LED in the first circuit 55 is shown at 76, and is connected via a current limiting resistor 77 to conductors 72 and 73. A by pass capacitor 78 is connected in parallel with the series-connected LED 76 and resistor 77. The parallel circuit is connected to the positive side of battery 62.

The independent second circuit 56 activated by the light from LED 76 comprises a phototransistor 79 whose collector 80 is connected to battery 63, and whose emitter 81 is connected via resistor 82 to second ground 61 and to the base input 83 of a transistor 84 whose collector 85 is connected to battery 63, and whose emitter 86 is connected to the coil 87 of a conventional relay 88, a diode 89, as shown, being included in the relay across the coil. A bypass capacitor 90 is connected across the base-emitter of transistor 84. The relay contacts 58 are connected to conductors 59 and 60, which together with conductor 72 terminate in the 3-pin connector 52.

Battery-monitoring third 64 and fourth 65 circuits are provided for testing the condition of each of the two batteries. Each of these circuits include a respective integrated circuit (IC) 92, 93 with external voltage-divider resistors 94-95 and 96-97, respectively, connected between their respective local ground 75, 61 and their respective batteries 62, 63 through respective switch contacts 98, 99 of common push-button test switch 70. Also, respective current-limiting resistors 100, 101 are connected in series with each of their respective test LED 68, 69.

The circuit illustrated operates under control of the finger-switch handpiece 34 as follows. Closing of either finger switch 38, 39 grounds at first ground 75 conductor 73 causing current supplied by first battery 62 to flow through LED 76, which is optically-coupled, but electrically-isolated from normally-OFF phototransistor 79. Light from the LED incident on phototransistor 79 turns it ON. The resultant current through resistor 82 from second battery 63 to second ground 61 produces a turn-ON base voltage for normally-OFF driver transistor 84. Its resultant emitter-collector current through coil 87 operates relay 88 closing contacts 58. From FIG. 1, it will be seen that contacts 58, via conductors 59 and 60, connectors 52, two jacks of mainframe connector 31 and mainframe conductors 102, 103, are connected in parallel with foot switch 27; hence, the mainframe 10 is switched into its operating mode. The RF currents under control of switch 15, generated along conductor 30 are conveyed through connectors 31 and 52 into the control unit 50 and along conductor 72. They then pass through connectors 51 and 46 onto conductor 42 into the handpiece and thence to the probe tip 40. Since the patient is grounded at mainframe RF ground 29, and the control unit grounds 75, 61 are isolated from mainframe ground, the RF currents flow to the patient and are not detoured via the finger switches 38, 39 to ground 75. When the finger switch is released, the mainframe returns to its standby mode.

As will be apparent from this description, either the foot switch or the handpiece finger switch can be employed to switch the mainframe from its standby to its operating mode. Retention of the foot switch control is an important advantage because certain procedures are preferably carried out using the foot control and other procedures using the handpiece control. The latter is generally employed for simple procedures, but the foot control is preferred by many users for more delicate cutting procedures where complete control, tactile sense and digital dexterity to move through soft tissue is needed. With both controls available at the patient site, the user can readily switch to either, or use both as preferred.

Another feature of the invention is the complete electrical isolation of the handpiece from the mainframe. This is achieved not only by the use of the LED-phototransistor photon isolator 76-79, but also by the electrical separation of the control unit circuit into two physically and electrically isolated building blocks powered by separate batteries. With reference to FIG. 2, the left-hand part of the circuit enclosed within the first dashed line box 105 is mounted on a first printed circuit board (PCB), and the right-hand part of the circuit enclosed within the second dashed line box 106 is mounted on a second PCB. Both PCB's are mounted, physically separated, within a suitable insulated sealed box or cabinet, eg. of plastic, which also houses the two batteries 62, 63. The connector 51 (FIG. 1) is mounted on one wall of the cabinet, and the connector 52 is mounted on a different wall of the cabinet. Thus, the control unit as a whole can be plugged into connector 31 on the mainframe front panel and supported thereby, the handpiece connector 46 then being plugged into connector 51, making for a compact system. As previously noted, the first PCB ground 75 or reference potential is isolated from the second PCB ground 61 or reference potential, and both grounds 75, 61 are isolated from patient ground 29. This novel isolation concept to prevent high power or high voltage feedback (AC line voltage or DC supply voltage for the RF oscillator) from the mainframe 10 to the handpiece 34 thus requires separate batteries for powering the two circuit halves 105, 106. The battery condition indicators 68, 69 are also mounted on a wall of the control unit cabinet, so as to be visible to the user, as is the common pushbutton test switch 70 so as to be accessible to the user. When the test switch 70 is operated by the user, both LEDs 68, 69 should light, indicating both batteries are satisfactory. If an LED fails to light, battery replacement is indicated.

Another feature of the invention is that each of the battery monitoring circuits 64, 65 can be custom controlled to turn on their respective LED at different threshold voltage values. For instance, it has been determined that, when each of the batteries is an alkaline battery with nominal 9 volt output, for highest reliability and to avoid erratic operation of the handpiece, the output voltage of battery 62 should not fall below 8 volts, whereas the output voltage of battery 63 should not fall below 7.4 volts. This is accomplished by ICs 92, 93 as controlled by suitable proportioning of their respective voltage dividers 94-95, 96-97. When test switch 70 is pressed, each of the ICs compares the output voltage of their respective battery against the different built-in threshold determined by their respective voltage dividers. If the output voltage is at or higher than the critical threshold, a connection is made from the LED cathode through the IC to the switch 70 contacts, and via the latter to the local ground, thus turning on the LED indicator. If either threshold condition is not met, the associated LED remains off indicating replacement of that battery is needed before commencing the surgical procedure.

As noted, the control unit is useful with most tube-type mainframes in which the mainframe ON-OFF switch activates the power supply and the tube filaments placing the mainframe in its standby mode, requiring only operation of a footswitch in or connected to the RF section to achieve the operating mode. Thus the unit can be used with commercially-available mainframes other than those described in U.S. Pat. No. 3,730,188. Such mainframes will however require a connector such as 31 wired up as shown or equivalently to perform the same functions. Should the pin configuration of such a mainframe connector not match that of connector 52, a suitable adaptor can be provided or a flexible cable substituted. As will be observed from the circuit of the FIG. 2 embodiment, the handpiece finger switches do not control the RF current generated. This is still accomplished by the current control knob 15 on the mainframe front panel. The connector 51 is standard and will accept most 1 or 2 finger switch handpiece connectors.

It will further be evident to those skilled in the art that, though some rewiring of the mainframe will be needed, the control unit described can be readily modified so that each of the two finger switches (normally labelled CUT and COAG) does in fact change the RF waveform coupled to the probe. This is readily achieved by providing an additional LED, corresponding to LED 76, in the first circuit 55 on PCB 105, an additional second circuit, which may be on the same PCB 106, including transistor counterparts to transistors 79, 84 positioned to respond to light from the additional LED, and an additional relay corresponding to relay 88 for operation by the additional second circuit. Then, a minor revision in connector 51 circuitry is needed so that when, for example, switch 38 is closed, only the LED 76 in the original first circuit 55 is grounded, activating only relay 88, whereas when switch 39 is closed, the counterpart additional LED only is grounded activating only the counterpart additional relay. The two relays will each need one set of contacts 58, connected in parallel, so that closing of either set will close the cathode circuit and turn on the RF oscillator, and will also each need a second set of contacts, connected to the connector 52 (which now will have to be a 7-pin connector). The modification of the mainframe circuitry is, essentially, to provide jacks and conductors at mainframe connector 31 which can be connected in parallel with two positions (CUT, COAG) of the switch 15 contacts (the switch 15 should desirably have an OFF or handpiece control position). With switch 15 contacts now in parallel with the second set of relay contacts and with switch 15 in its OFF position activation of the handpiece CUT button will not only turn on the RF oscillator but also control the power supply circuitry to produce the CUT waveform, and similarly activation of the COAG button would also turn on the RF oscillator and simultaneously execute the power supply control function previously performed by control 15 to produce the COAG waveform. The circuitry for accomplishing the above is simple and will be evident to the skilled circuit designer and further details are therefore unnecessary.

The same isolation benefits as is the first-described embodiment are still obtained with the above-described modification. Thus, the handpiece will be coupled to the RF current-carrying conductors, which presents no potential patient harm, and, only to the first PCB 105, and thus is completely isolated by any direct connection from the AC line voltage and high DC voltages in the mainframe, which latter remains connected via the relay contacts only to the second PCB 106. The user operation of the non-isolated footswitch 27 presents no feedback problem. As a result, any DC voltage feedback from the mainframe to the handpiece is prevented even though, electrically speaking, the finger switches are operatively coupled in parallel with the foot switch, which is connected to the mainframe, in both the preferred embodiment and the modification, and also with the control switch contacts in the modification.

Attention is also directed to the limiting resistors 77, 100, 101 in series with each of their respective LED. These prevent overloading of the LED and prolong its life.

The control unit described is useful with electro-surgery equipment designed for use in the medical, dental and veterinary fields, and provides a relatively inexpensive, compact device offering increased reliability and voltage protection and the novel functions as hereinbefore described. It increases the capabilities of existing equipment without requiring replacement or undue modification.

To aid those skilled in this art in reproducing the preferred embodiment, information concerning values and functions of the significant components are: ICs 92,93, eg. LM 3905, are conventional voltage comparator circuits; resistors 94 and 95 have values in the ratio of 3:1, and 96 and 97 in the ratio of 2.7:1 to achieve the mentioned thresholds; resistors 77=220 ohms and resistors 100, 101=500 ohms; LED 76 and phototransistor 79 is available commercially as a matched pair as a photon-coupled optical isolator; transistor 84 is a standard NPN driver transistor; the remaining components are standard and their values and functions will be evident to those skilled in circuit design.

While our invention has been described in connection with specific embodiments thereof, those skilled in the art will recognize that various modifications are possible within the principles enunciated herein and thus the present invention is not to be limited to the specific embodiments disclosed.

What is claimed is:

1. A self-powered control unit for interfacing a finger switch handpiece probe having a cable terminated by a handpiece connector to a mainframe electrosurgical instrument having an RF generator employing a filament-heated electron tube RF oscillator circuit activated by a DC voltage derived from an AC line voltage operated power supply and having a mainframe connector for receiving a control unit connector, said mainframe instrument further having an ON-OFF switch for switching on the power supply and for supplying electric current to the tube filament to heat same to place the mainframe instrument in a standby mode, said mainframe instrument further having a foot switch connected to the mainframe instrument and electrically connected to the RF oscillator circuit in such manner that when the foot switch is activated the RF oscillator is switched on generating RF electrosurgical currents thereby placing the mainframe instrument in its operating mode; said control unit comprising a first connector for receiving the handpiece connector and a second connector for connecting said control unit to the mainframe connector, said control unit further having a first circuit connected to the first connector and comprising a light-emitting device connected in series with the handpiece probe finger switch when the handpiece probe and control unit are connected whereby operation of the finger switch causes the light-emitting device when powered to emit light, said control unit further having a second circuit connected to the second connector and comprising a light-sensitive active device located to receive light emitted by the light-emitting device and upon so receiving such light being converted from a normally OFF condition to an active ON condition whereby said handpiece probe is electrically isolated from the mainframe instrument AC line voltage, means connected to the first and second circuits for powering same; characterized by said control unit comprising:

(a) means in said second circuit for connecting said active device to the second connector in such manner that when the control unit is connected to the mainframe instrument, the active device is coupled in parallel with the foot switch whereby the mainframe instrument can be switched into its operating mode by actuating either the finger switch or the foot switch, (b) means for electrically isolating the control unit first connector from its second connector to prevent harmful power feedback of AC line voltage or DC voltage from the mainframe instrument to the handpiece probe via the control unit when connected together, (c) said powering means comprising a first battery connected in the first circuit and a second battery connected in the second circuit, and (d) battery monitoring circuits coupled to the first and second circuits and including a battery condition indicator operable to indicate battery deterioration below a threshold voltage indicating battery replacement is needed.

2. A self-powered control unit as claimed in claim 1 characterized by said light-emitting device and battery condition indicator being LEDs, and a current-limiting resistor being connected in series with each of the LEDs.

3. A self-powered control unit as claimed in claim 1 characterized by said battery monitoring circuits including third and fourth circuits, said third circuit being connected to the first battery which powers the first circuit, said fourth circuit being connected to the second battery which powers the second circuit, said battery monitoring circuits functioning to compare the battery output voltage of their respective battery to a built-in threshold voltage and activating the battery indicator when the threshold voltage is met or exceeded.

4. A self-powered control unit as claimed in claim 3 characterized by the first and third circuits share a common first reference potential, and the second fourth circuits share a common second reference potential, said first and second reference potentials being electrically isolated from each other.

5. A self-powered control unit as claimed in claim 4 characterized by the threshold voltages for the third and fourth circuits being different from each other, said first and second batteries having the same nominal output voltage.

6. A self-powered control unit as claimed in claim 3 characterized by said monitoring circuits comprising means for establishing a threshold voltage, and means connected to the threshold voltage establishing means for activating the battery condition indicator when the battery output voltage exceeds the threshold voltage.

7. A self-powered control unit as claimed in claim 1 characterized by said electrical isolating means comprising means for electrically separating the first from the second circuit, the first and second batteries separately powering the first and the second circuits to maintain their electrical separation.

8. A self-powered control unit as claimed in claim 7 characterized by said electrically separating means comprising first and second isolated PCBs, the first circuit being mounted on the first PCB and the second circuit being mounted on the second PCB, whereby the first connector is DC voltage isolated from the second connector though the latter is DC voltage connected to the mainframe instrument.

9. A self-powered control unit as claimed in claim 8 characterized by the first and second PCBs and the batteries are housed in a common cabinet adapted to plug into the mainframe instrument.

10. In combination, a finger switch handpiece probe having a cable terminated by a handpiece connector, a mainframe electrosurgical instrument having an RF generator employing a filament-heated electron tube RF oscillator circuit activated by a DC voltage derived from an AC line voltage operated power supply and having a mainframe connector, and a self-powered control unit for interfacing the handpiece probe to the mainframe instrument; said mainframe instrument further having an ON-OFF switch for switching on the power supply and for supplying electric current to the tube filament to heat same to place the mainframe instrument in a standby mode, said mainframe instrument further having a foot switch connected to the mainframe instrument and electrically connected to the RF oscillator circuit in such manner that when the foot switch is activated the RF oscillator is switched on generating RF electrosurgical currents thereby placing the mainframe instrument in its operating mode; said control unit comprising a first connector receiving the handpiece connector and a second connector connecting said control unit to the mainframe connector, said control unit further having a first circuit connected to the first connector and comprising a light-emitting device connected in series with the handpiece probe finger switch when the handpiece probe and control unit are connected whereby operation of the finger switch causes the light-emitting device when powered to emit light, said control unit further having a second circuit connected to the second connector and comprising a light-sensitive active device located to receive light emitted by the light-emitting device and upon so receiving such light being converted from a normally OFF condition to an active ON condition whereby said handpiece probe is electrically isolated from the mainframe instrument AC line voltage, means connected to the first and second circuits for powering same; said control unit further comprising means in said second circuit for connecting said active device to the second connector in such manner that when the control unit is connected to the mainframe instrument, the active device is coupled in parallel with the foot switch whereby the mainframe instrument can be switched into its operating mode by actuating either the finger switch or the foot switch, means for electrically isolating the control unit first connector from its second connector to prevent harmful power feedback of AC line voltage or DC voltage from the mainframe instrument to the handpiece probe via the control unit when connected together; said powering means comprising a first battery connected in the first circuit and a second battery connected in the second circuit; said control unit further comprising battery monitoring circuits coupled to the first and second circuits and including a battery condition indicator operable to indicate battery deterioration below a threshold voltage indicating battery replacement is needed.

11. A self-powered control unit for interfacing a finger switch handpiece probe having a cable terminated by a handpiece connector to a mainframe electrosurgical instrument having an RF generator employing a filament-heated electron tube RF oscillator circuit activated by a DC voltage derived from an AC line voltage operated power supply and having a mainframe connector for receiving a control unit connector, said mainframe instrument further having an ON-OFF switch for switching on the power supply and for supplying electric current to the tube filament to heat same to place the mainframe instrument in a standby mode, said mainframe instrument further having a foot switch connected to the mainframe instrument and electrically connected to the RF oscillator circuit in such manner that when the foot switch is activated the RF oscillator is switched on generating RF electrosurgical currents thereby placing the mainframe instrument in its operating mode; said control unit comprising a housing and a first connector on the housing for receiving the handpiece connector and a second connector on the housing for connecting said control unit to the mainframe connector, said control unit further having a first circuit connected to the first connector and comprising a light-emitting device connected in series with the handpiece probe finger switch when the handpiece probe and control unit are connected whereby operation of the finger switch causes the light-emitting device when powered to emit light, said control unit further having a second circuit connected to the second connector and comprising a light-sensitive active device located to receive light emitted by the light-emitting device and upon so receiving such light being converted from a normally OFF condition to an active ON condition whereby said handpiece probe is electrically isolated from the mainframe instrument AC line voltage, means connected to the first and second circuits for powering same; characterized by said control unit further comprising:
(a) means in said second circuit for connecting said active device to the second connector in such manner that when the control unit is connected to the mainframe instrument, the active device is coupled in parallel with the foot switch whereby the mainframe instrument can be switched into its operating mode by actuating either the finger switch or the foot switch, and
(b) means for electrically isolating the control unit first connector from its second connector to prevent harmful power feedback of AC line voltage or DC voltage from the mainframe instrument to the handpiece probe via the control unit when connected together, said electrically isolating means including first and second PCBs electrically isolated within the housing, the first circuit being mounted on the first PCB and the second circuit being mounted on the second PCB, whereby the first connector is DC voltage isolated from the second connector though the latter is DC voltage connected to the mainframe instrument.

12. A self-powered control unit as claimed in claim 11 characterized by the powering means comprising means for powering by separate batteries the first and the second circuits to maintain their electrical separation.

13. A self-powered control unit as claimed in claim 11 and further comprising separate battery monitoring circuits coupled, respectively, to the first and second circuits for monitoring the condition of the separate batteries and for indicating when battery replacement is needed.

* * * * *